US012014293B2

(12) United States Patent
Min et al.

(10) Patent No.: US 12,014,293 B2
(45) Date of Patent: Jun. 18, 2024

(54) ELECTRONIC HEALTH RECORD DATA SYNTHESIZATION

(71) Applicant: International Business Machines Corporation, Armonk, NY (US)

(72) Inventors: Xu Min, Beijing (CN); Yi Qin Yu, Beijing (CN); Jing Mei, Beijing (CN); Yuan Zhou, Beijing (CN); Shao Chun Li, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 462 days.

(21) Appl. No.: 16/941,561

(22) Filed: Jul. 29, 2020

(65) Prior Publication Data

US 2022/0036981 A1 Feb. 3, 2022

(51) Int. Cl.
*G06F 21/62* (2013.01)
*G06F 17/18* (2006.01)
*G06N 3/0455* (2023.01)
*G06N 3/047* (2023.01)
*G06N 7/01* (2023.01)
*G16H 10/60* (2018.01)

(52) U.S. Cl.
CPC ............. *G06N 7/01* (2023.01); *G06F 17/18* (2013.01); *G06F 21/6245* (2013.01); *G06N 3/0455* (2023.01); *G06N 3/047* (2023.01); *G16H 10/60* (2018.01)

(58) Field of Classification Search
CPC ...... G06N 7/005; G06N 3/0472; G06F 17/18; G06F 21/6245; G16H 10/60
See application file for complete search history.

(56) References Cited

U.S. PATENT DOCUMENTS

2018/0018590 A1* 1/2018 Szeto ............... G16H 40/20
2019/0087604 A1* 3/2019 Antonatos ........... G06F 21/6245

FOREIGN PATENT DOCUMENTS

| EP | 3576020 A1 | 12/2019 | |
| WO | 2019122854 A1 | 6/2019 | |
| WO | WO-2020064990 A1 * | 4/2020 | ........... G06K 9/4628 |

OTHER PUBLICATIONS

Meng, Rui. Temporal Data Models via Stochastic Process. University of California, Santa Cruz, Jun. 2020. (Year: 2020).*
Zhang, ChunMei et al. DPETS: A Differently Private ExtraTrees. 13th International Conference on Computational Intelligence and Security. 2017. (Year: 2017).*
Goncalves, Andre, et al. "Generation and evaluation of synthetic patient data." BMC medical research methodology 20.1 (2020): 1-40. (Year: 2020).*

(Continued)

*Primary Examiner* — Joshua B Blanchette
*Assistant Examiner* — Chance L Smith
(74) *Attorney, Agent, or Firm* — Peter J. Edwards

(57) ABSTRACT

The present disclosure relates to a method, system and computer program product for electronic health record (EHR) data synthetization. According to the method, an original EHR dataset X is captured. A latent space Z is generated from the original EHR dataset X, wherein dimensionality of Z is lower than that of X. A stochastic process prior module is applied to the latent space Z. Synthetic EHR dataset X' is reconstructed from the latent space Z after being applied with the stochastic process prior.

20 Claims, 7 Drawing Sheets

(56) References Cited

OTHER PUBLICATIONS

Jordon, James, Jinsung Yoon, and Mihaela Van Der Schaar. "PATE-GAN: Generating synthetic data with differential privacy guarantees." International conference on learning representations. 2018. (Year: 2018).*
Lawrence, Neil. "Gaussian process latent variable models for visualisation of high dimensional data." Advances in neural information processing systems 16 (2003). (Year: 2003).*
Wang, Gang, et al. "Latent process model for manifold learning." 17th IEEE International Conference on Tools with Artificial Intelligence (ICTAI'05). IEEE, 2005. (Year: 2005).*
Source code for "Temporal Data Models via Stochastic Process." UC Santa Cruz. Meng, R. (2020). Available at: view-source:https://escholarship.org/uc/item/1283t4b3 (Year: 2020).*
XML sitemap for "eScholarship University of California." Available at: https://escholarship.org/siteMapItem-02.xml (Year: 2020).*
Salim Jr, Ally. "Synthetic patient generation: A deep learning approach using variational autoencoders." arXiv preprint arXiv:1808.06444 (2018). (Year: 2018).*
Vardhan, L. Vivek Harsha, and Stanley Kok. "Generating privacy-preserving synthetic tabular data using oblivious variational autoencoders." Proceedings of the Workshop on Economics of Privacy and Data Labor at the 37 th International Conference on Machine Learning (ICML). Jul. 18, 2020. (Year: 2020).*
Wan, Zhiqiang, Yazhou Zhang, and Haibo He. "Variational autoencoder based synthetic data generation for imbalanced learning." 2017 IEEE symposium series on computational intelligence (SSCI). IEEE, 2017. (Year: 2017).*
Yan, Chao, et al. "Generating electronic health records with multiple data types and constraints." AMIA annual symposium proceedings. vol. 2020. American Medical Informatics Association, Mar. 23, 2020. (Year: 2020).*
Becker-Ehmck, Philip, Jan Peters, and Patrick Van Der Smagt. "Switching linear dynamics for variational bayes filtering." International conference on machine learning. PMLR, 2019. (Year: 2019).*
Biswal, Siddharth, et al. "EVA: Generating longitudinal electronic health records using conditional variational autoencoders." Machine Learning for Healthcare Conference. PMLR, 2021. (Year: 2021).*
Nikolentzos, Giannis, et al. "Synthetic electronic health records generated with variational graph autoencoders." npj Digital Medicine 6.1 (2023): 83. (Year: 2023).*
"CMS 2008-2010 Data Entrepreneurs' Synthetic Public Use File," Centers for Medicare & Medicaid Services, accessed Jul. 20, 2020, 4 pages. <https://www.cms.gov/research-statistics-data-and-systems/downloadable-public-use-files/synpufs/de_syn_puf>.
"Mostly Generate," Mostly AI, accessed Jul. 20, 2020, 7 pages. <https://mostly.ai/generate/>.
"Synthetic Patient Generation," Synthea, accessed Jul. 20, 2020, 12 pages. <https://synthetichealth.github.io/synthea/.
Choi et al., "Generating Multi-label Discrete Patient Records using Generative Adversarial Networks," Proceedings of Machine Learning for Healthcare 2017, Aug. 19, 2017, 20 pages. <http://proceedings.mlr.press/v68/choi17a/choi17a.pdf>.
Dahmen et al., "SynSys: A Synthetic Data Generation System for Healthcare Applications.," Sensor 19(5): 1181, Mar. 8, 2019, 11 pages. <https://www.researchgate.net/publication/331613205_SynSys_A_Synthetic_Data_Generation_System_for_Healthcare_Applications>.
Dash et al., "Synthetic Event Time Series Health Data Generation," GroundAI, Nov. 14, 2019, 5 pages. <https://www.groundai.com/project/synthetic-event-time-series-health-data-generation/1>.
Frigerio et al., "Differentially Private Generative Adversarial Networks for Time Series, Continuous, and Discrete Open Data," arXiv.org, Jan. 8, 2019, 18 pages. <https://arxiv.org/abs/1901.02477>.
Mell et al., "The NIST Definition of Cloud Computing," Recommendations of the National Institute of Standards and Technology, U.S. Department of Commerce, Special Publication 800-145, Sep. 2011, 7 pages.
Park et al., "PeGS: Perturbed Gibbs Samplers that Generate Privacy-Compliant Synthetic Data," Transactions on Data Privacy, vol. 7, Issue 3, Dec. 2014, pp. 253-282. <https://www.semanticscholar.org/paper/PeGS%3A-Perturbed-Gibbs-Samplers-that-Generate-Data-Park-Ghosh/5be236807dd5d2b3934b80b1945f10f2f8c0a7e4>.
Pimentel et al., "Modelling Patient Time-Series Data from Electronic Health Records using Gaussian Processes," Semantic Scholar, 2013, 4 pages. <https://pdfs.semanticscholar.org/5fb9/98018834eab31ec33b5326954672a6cb9735.pdf >.
Sartor, "Explaining Differential Privacy in 3 Levels of Difficulty," Aircloak, May 10, 2019, 6 pages. <https://aircloak.com/explaining-differential-privacy/>.
Schiff et al., "Efficient Enriching of Synthesized Relational Patient Data with Time Series Data," Procedia Computer Science, vol. 141, 2018, pp. 531-538. <https://www.sciencedirect.com/science/article/pii/S1877050918317794>.
Tiu, "Understanding Latent Space in Machine Learning," Towards Data Science, Feb. 4, 2020, 13 pages. <https://towardsdatascience.com/understanding-latent-space-in-machine-learning-de5a7c687d8d>.

* cited by examiner

ELECTRONIC HEALTH RECORD DATA SYNTHESIZATION

BACKGROUND

The present disclosure generally relates to data processing, and more specifically, relates to methods, systems or computer program products for EHR data synthetization.

An electronic health record (EHR), also known as an electronic medical record (EMR), is a collection of electronically stored information about an individual patient's medical history. EHR data may contain a broad range of data, including demographics, medical history, medication history, allergies, immunization records, laboratory test results, radiology images, vital signs, personal statistics such as age and weight, and billing information. Many commercial EHR systems combine data from a number of healthcare services and providers, such as clinical care facilities, laboratories, radiology centers, and pharmacies. Those EHR data, which are usually time series data, i.e., a series of data points indexed in time order, are one of the most important data sources for healthcare data analytics. Those EHR data can be used for both academic and commercial services/systems. However, there are also a lot of challenges remaining for time series data to be used in real-world analysis tasks.

SUMMARY

Aspects of an embodiment of the present disclosure disclose a method, computer program product and/or system that performs the following operations (not necessarily in the following order) for EHR data synthetization. A processor captures an original EHR dataset X. A processor generates a latent space Z from the original EHR dataset X, wherein dimensionality of Z is lower than that of X. A processor applies a stochastic process prior to the latent space Z. A processor reconstructs synthetic EHR dataset X' from the latent space Z after being applied with the stochastic process prior.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Figure 1:
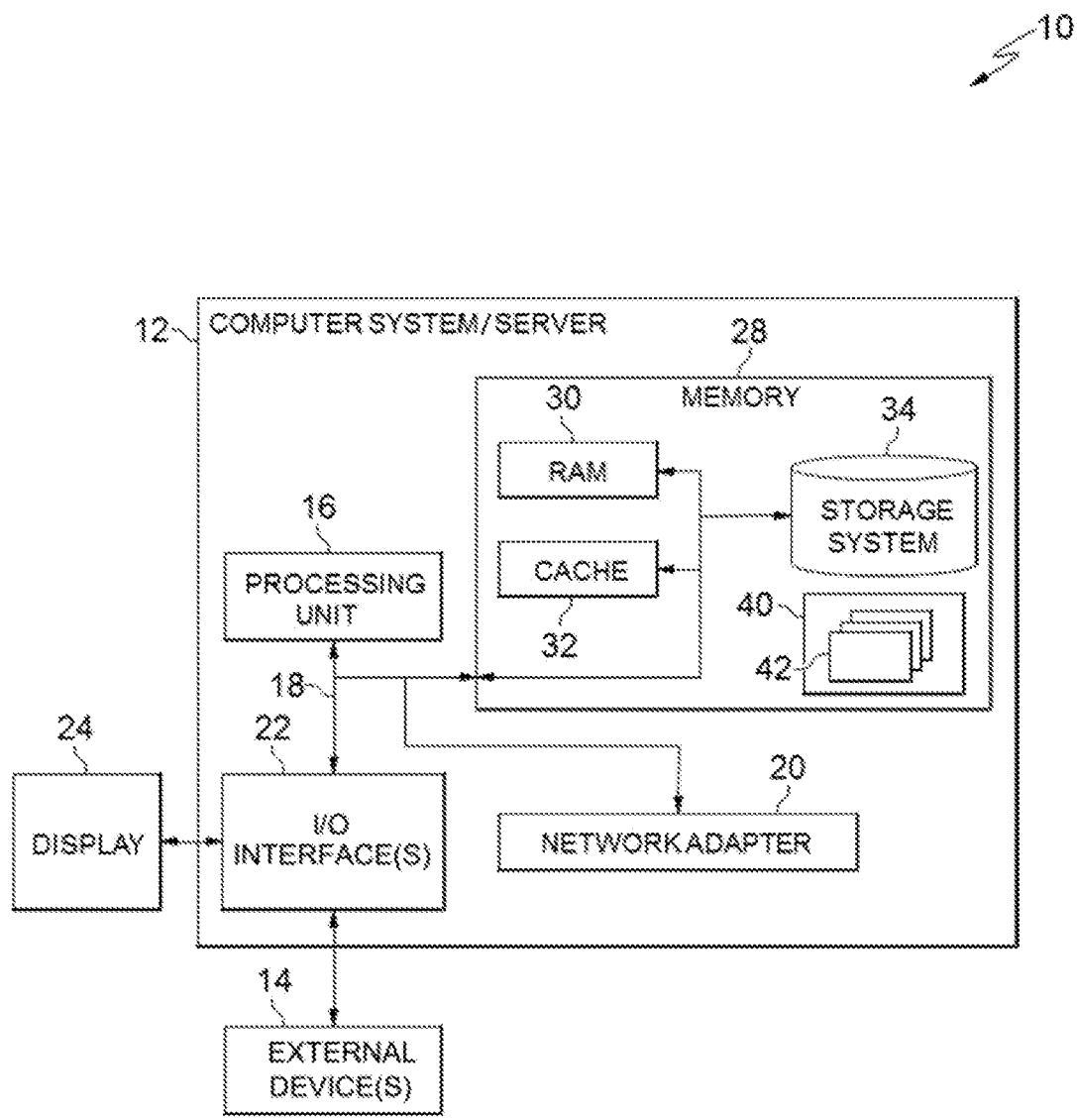
FIG. 1 depicts a cloud computing node according to an embodiment of the present disclosure.

Some embodiments will be described in more detail with reference to the accompanying drawings, in which the embodiments of the present disclosure have been illustrated. However, the present disclosure can be implemented in various manners, and thus should not be construed to be limited to the embodiments disclosed herein. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

It is to be understood that although this disclosure includes a detailed description on cloud computing, implementations of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the disclosure described herein. Regardless, cloud computing node 10 is capable of being implemented and/or performing any of the functionality set forth hereinabove.

In cloud computing node 10 there is a computer system/server 12 or a portable electronic device such as a communication device, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the disclosure as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
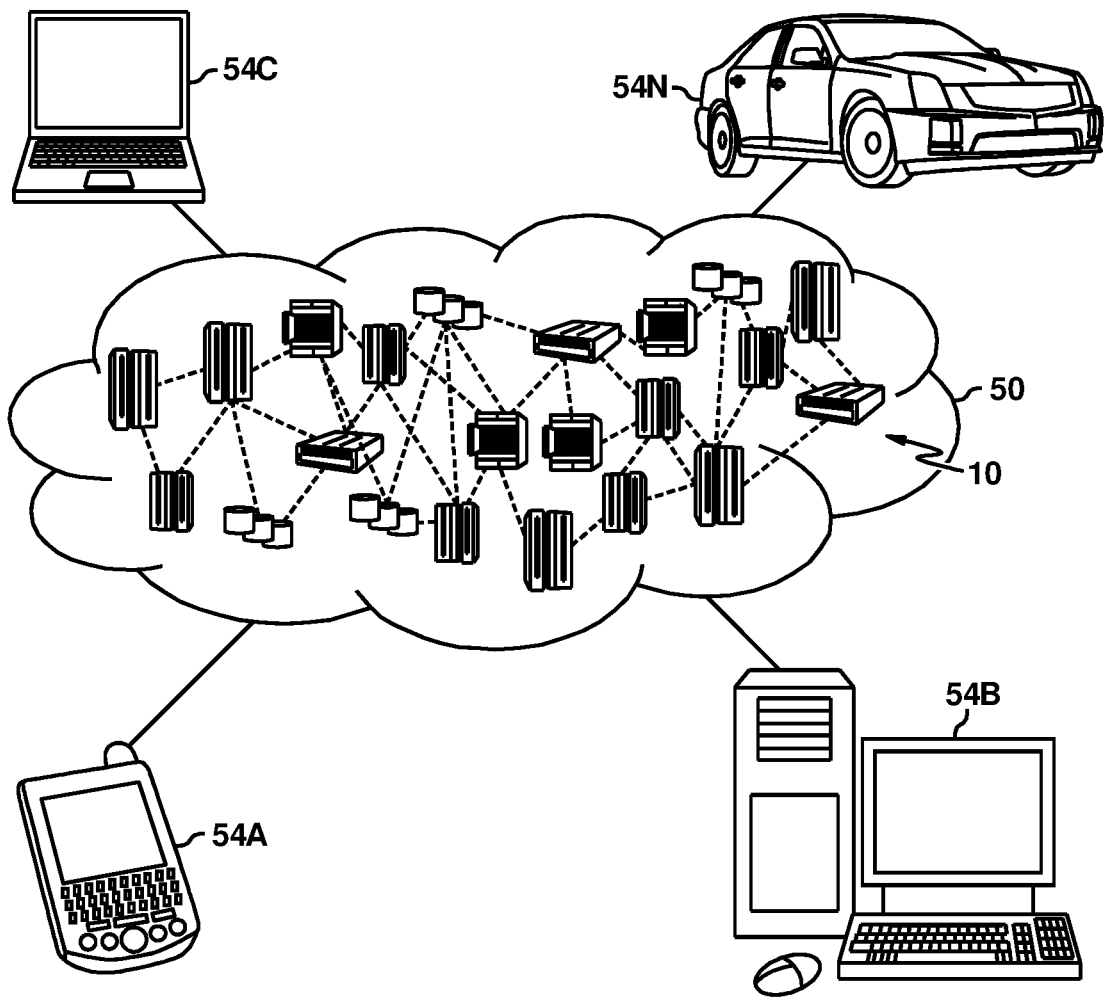
FIG. 2 depicts a cloud computing environment according to an embodiment of the present disclosure.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
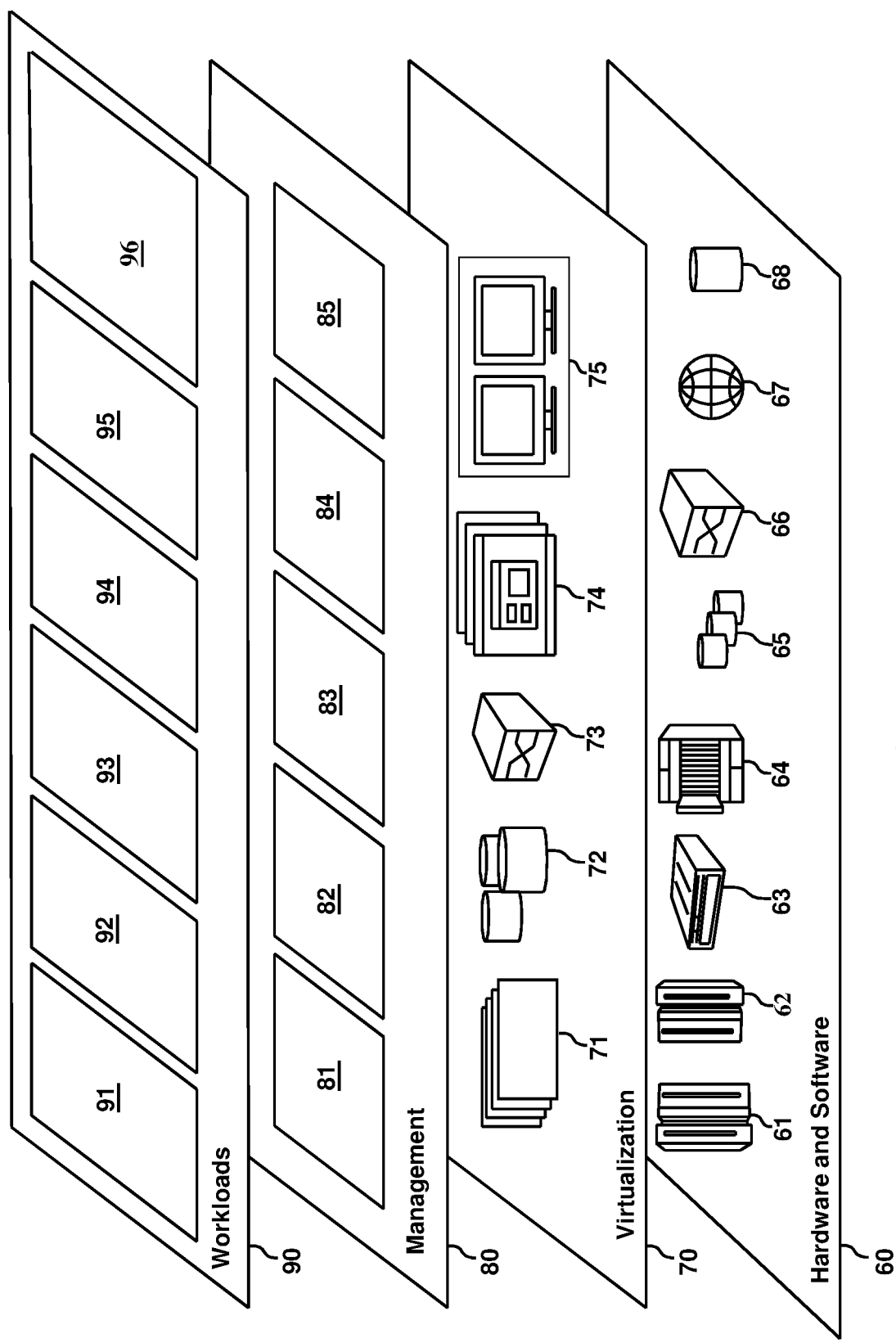
FIG. 3 depicts abstraction model layers according to an embodiment of the present disclosure.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the disclosure are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and electronic health record (her) data synthetization 96.

EHR data can be the basis of various data analysis tasks, such as academic research, commercial service, system development and healthcare application implementation, etc. However, because of the privacy issue and limited data size of original EHR data, original EHR data normally cannot be directly used. Instead, synthetization of EHR data is needed to transform and expand the size of the original EHR data. Synthetic EHR data which are derived from the original EHR data should keep the fidelity of the original EHR data. For example, the changing trend/pattern or characteristics of synthetic EHR data should approximate that of the original EHR data. Meanwhile privacy of the original EHR data should be protected, so that others cannot easily detect the original EHR data from the synthetic EHR data. Additionally, the data size of original EHR data is better to be expanded when the synthetic EHR data is generated, to meet a growing demand for using a large number of data. Embodiments of this disclosure can help to address at least one of the above problems.

Figure 4:
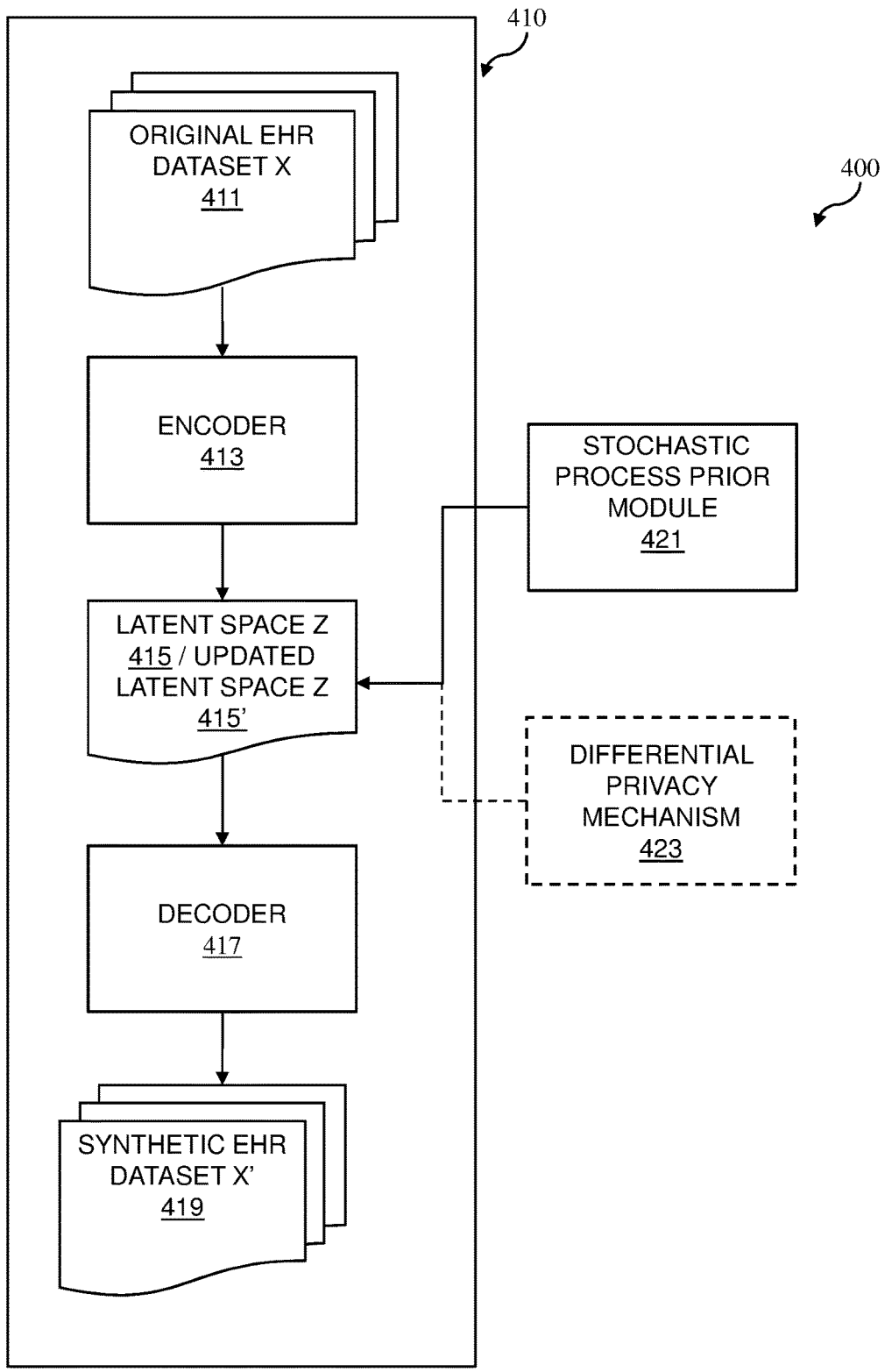
FIG. 4 depicts a diagram of EHR data synthetization in accordance with an embodiment of the present disclosure.

FIG. 4 depicts a system diagram for EHR data synthetization in accordance with embodiments of the present disclosure. System 400 includes variational autoencoder (VAE) module 410 and a stochastic process prior module 421. Additionally, system 400 also includes differential privacy mechanism module 423. VAE module 410 further includes original EHR dataset X 411, encoder 413, latent space Z 415, decoder 417, synthetic EHR dataset X' 419.

Generally, a VAE is an autoencoder whose encodings distribution is regularized during the training in order to ensure that its latent space has good properties to generate new data. A VAE ensures only the main structured part of the information can go through and be reconstructed. A VAE comprising both an encoder 413 and a decoder 415 can be trained to minimize the reconstruction error between the encoded-decoded synthetic EHR dataset X' 419 and the original EHR dataset X 411. After the original ERH dataset X 411 is fed into the encoder 413, the encoded-decoded output, synthetic EHR dataset X'419, will be compared with the original ERH dataset X 411 and backpropagate the error through the VAE module 410 to update the weights of the networks to train the VAE module 410. It is well understood that the variational autoencoding can be achieved based on any existing or newly developed technology.

Specifically, encoder 413 can store all of the original EHR dataset X 411's relevant features in a compressed representation, i.e. latent space Z 415, so that there is enough information in that compressed form such that the VAE module 410 can "accurately" reconstruct it to synthetic EHR dataset X' 419. Encoder 413 can perform dimensionality reduction which is a process of reducing the number of features that describe some data. So that dimension in latent space Z 415 will be lower than that of original EHR dataset X 411. Dimensionality reduction can be understood as data compression where the encoder 413 compresses the original EHR data X 411 into the latent space Z, whereas the decoder 417 decompress them to reconstruct synthetic EHR dataset X' 419. Of course, a part of the information could be lost during the encoding process and cannot be reconstructed when decoding.

For the purpose of simplicity, a simple example will be used below to illustrate EHR data and how it could be processed in system 400. Suppose a patient visited a hospital for four times in a year and obtained four sets of EHR data via physical examination including blood pressure, blood sugar and high density lipoproteins (HDL) cholesterol. The normal range of above three measures are illustrated below in Table 1.

TABLE 1

| Measures | Normal range |
| --- | --- |
| High blood pressure | <120 mm Hg |
| Fasting blood sugar | <5.6 mmol/L |
| HDL cholesterol | >1.04 mmol/L |

Suppose the examination results of the patient are shown below in Table 2.

TABLE 2

| | 1$^{st}$ exam | 2$^{nd}$ exam | 3$^{rd}$ exam | 4$^{th}$ exam |
| --- | --- | --- | --- | --- |
| High blood pressure(mm Hg) | 140 | 110 | 115 | 110 |
| Fasting blood sugar (mmol/L) | 6.3 | 6.1 | 5.9 | 5.5 |
| HDL cholesterol (mmol/L) | 1.03 | 1.01 | 1.13 | 1.19 |

Original EHR dataset X 411 of the patient could be shown as following:

$$x_{ij} = \begin{bmatrix} \text{high blood pressure} \\ \text{fasting blood sugar} \\ HDL \text{ cholesterol} \\ \vdots \end{bmatrix}$$

Wherein "i" represents the patient "i", which could be specifically represented by, for example, ID No.; "j" represents the times of examination; $x_{ij}$ represents the EHR data of patient i on the jth time of examination. The patient i's original EHR dataset 411, therefore, can be shown as following based on the results in Table 2:

$$x_{11} = \begin{bmatrix} 140 \\ 6.3 \\ 1.03 \end{bmatrix}$$

$$x_{12} = \begin{bmatrix} 110 \\ 6.1 \\ 1.01 \end{bmatrix}$$

$$x_{13} = \begin{bmatrix} 115 \\ 5.9 \\ 1.13 \end{bmatrix}$$

$$x_{14} = \begin{bmatrix} 110 \\ 5.5 \\ 1.19 \end{bmatrix}$$

Here a $x_{ij}$ is representative of a 3×1 matrix. It could be understood that $x_{11}$ has three measures abnormal, while $x_{12}$ has two measures abnormal, $x_{13}$ has only one measure abnormal and $x_{14}$ has no measure abnormal. This could be a very typical process that after certain kind of treatment the patient became healthy from unhealthy.

It is also understood that the above example EHR data is provided for illustration purpose without suggesting any limitation. EHR data having other dimensionality and/or meanings can be used. Apart from discrete values illustrated above, EHR data can also be represented by continuous values (for example, continuously monitored blood pressure of a patient can generate continuous EHR data). Actually, the EHR data used in practice is normally much more complicated than the example shown above.

In the latent space Z 415, dimensionality of the original EHR dataset X 411 will be reduced. Reduced dimensionality can be set in advance as a number lower than that of the original EHR dataset X 411. For example, above 3×1 dataset X can be reduced into 1×1 dataset Z. Although current encoder 413 can generate latent space Z 415 according to pre-set dimensionality, it has no knowledge about the meaning of this reduced dimensionality, therefore it cannot generate latent space Z 415 by considering characteristics of the original EHR dataset X 411 in time order.

Continue to use the example shown in Table 2. The patient cannot be cured suddenly after the first time he visited the hospital. Instead, all the measures are gradually turned back to normal after three times of visiting the hospital. Specifically, at the first examination, all three measures of the patients were abnormal, at the second examination, two measures of the patients remained abnormal, at the third examination, one measure of the patient remained abnormal, and at the fourth check, all measures of the patient turned to normal.

Z values in the latent space Z 415 could be represented by $z_{ij}$, wherein "i" represents patient i, and "j" represents the times of examination. In theory, if the latent space Z 415 can be set manually, and Table 3 illustrates example rules for setting the latent space Z 415.

TABLE 3

| Values of $z_{ij}$ | Rules |
|---|---|
| 0 | No measure abnormal |
| 1 | One measure abnormal |
| 2 | Two measures abnormal |
| 3 | Three measures abnormal |

Based on rules shown in Table 3 above, $z_{ij}$ could be shown as following:

$z_{11}=[3]$
$z_{12}=[2]$
$z_{13}=[1]$
$z_{14}=[0]$
or $$z_{1j}{}^{4}_{j=1} = [3,2,1,0]$$

However, current encoder 413 has no knowledge regarding to how to set up the latent space Z 415 as rules illustrated in Table 3, or in other words, the current encoder 413 cannot attach any physical meaning to the latent space Z 415. The latent space Z 415 can be generated without considering any characteristic of time series. The generated Z values, therefore, may not be in line with the characteristics of time series. For example, it may not be $$z_{1j}{}^{4}_{j=1} = [3,2,1,0],$$

instead it could be $$z_{1j}{}^{4}_{j=1} = [3,0,1,0].$$

Sometimes, such Z values could be unrealistic, because measures of chronic disease of a patient normally will not fluctuate violently. Such generated Z values, therefore, cannot represent real time series, and the reconstructed synthetic EHR dataset X' 419 cannot reflect real change of data over the time.

In order to resolve one of above problems, according to embodiments of the present disclosure, a stochastic process prior module 421 could be used to calibrate the latent space Z 415 by considering characteristics of time series. For example, Z values will not fluctuate violently, but instead they will change gradually over time. Therefore, Z values that have a low probability to happen in reality will be abandoned, while Z values that have a high probability to happen in reality will be kept. The stochastic process prior module 421 could be, for example, Markov process prior module for discrete data, and Gaussian process prior R module for continuous data. It would be appreciated by a person skilled in the art that other types of process prior modules (either existing or newly developed in the future) can also be used for processing the discrete or continuous data. It should be understood by those skilled in the art that, gradually changed Z values are only illustrated as an example of characteristics of time series without suggesting any limitation, and other kinds of characteristics can also be adopted depending on the nature of EHR data, such as continuously increasing, continuously decreasing, changes following a certain pattern, etc.

Hereinafter, illustration will be given with regards to Markov process prior and Gaussian process prior separately. Parameters of the Markov process prior includes state space S and transition rate matrix Q. The state space S indicates all the available states of data, while, the transition rate matrix Q indicates the probability of transmitting from one state to another (including the original state itself). The state space S could include, for example, data to be selected from space S [0, 1, 2, 3]. The transition rate matrix Q could be, for example, shown in following Table 4.

TABLE 4

| | From | | | |
|---|---|---|---|---|
| To | 0 | 1 | 2 | 3 |
| 0 | 70% | 15% | 5% | 1% |
| 1 | 25% | 70% | 30% | 9% |
| 2 | 4% | 10% | 60% | 40% |
| 3 | 1% | 5% | 5% | 50% |

According to Table 4, the probability of remaining at the state "0" is the 70%, the probability of changing the state from "0" to "1" is 25%, the probability of changing the state from "0" to "2" is 4%, and the probability of changing the state from "0" to "3" is 1%, etc. From various probabilities shown in the Table 4 above, it is more likely to stay at one state or change to an adjacent state, while it is unlikely to change from one state to a non-adjacent state. Or in other words, measures of a patient normally will change gradually, not sharply.

Both the state space S and the transition rate matrix Q can be generated based on knowledge of domain expert or automatically based on study of the original EHR dataset X 411. It would be also understood by the person skilled in the art that Table 4 above only provides an example to illustrate transition rate matrix Q without suggesting any limitation. Applying the Markov process prior to the latent space Z 415 is to ensure the latent space Z 415 will not include violently fluctuated data, such as $$z_{1j}{}^{4}_{j=1} = [3,0,1,0].$$

The stochastic process prior module 421 can ensure that the latent space Z 415 will not include large fluctuations from the creation of latent space Z 415. In the circumstance that the original EHQ dataset 411 is discrete values as illustrated above, the stochastic process prior module 421 can be Markov process prior. Once parameters for setting up Markov process prior can be received, including state space S and a transition rate matrix Q, then Markov process prior can be applied to the latent space Z 415 based on the received state space S, the transition rate matrix Q. The state space S and the transition rate matrix Q could be decided based on the domain knowledge.

By applying Markov process prior to the latent space Z 415, large fluctuation of latent space Z 415 can be avoided, and the synthetic EHR dataset X' 419 can approximate, but not be the same as, the original EHR dataset X 411.

For continuous EHR dataset X 411, Gaussian process prior can be used in the stochastic process prior module 421 to calibrate latent space Z 415. Parameters needed for Gaussian process prior include means and covariances. The means and covariances can be set as, for example, 1.5 and 1 respectively. It should be understood that means and covariances of Gaussian process prior can be changed based on tolerance of fluctuation.

Figure 5A:
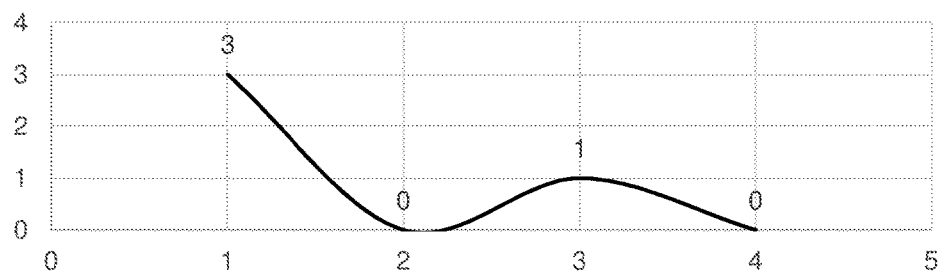
FIG. 5A depicts a diagram of example Z values before the Gaussian process prior in accordance with an embodiment of the present disclosure.
Figure 5B:
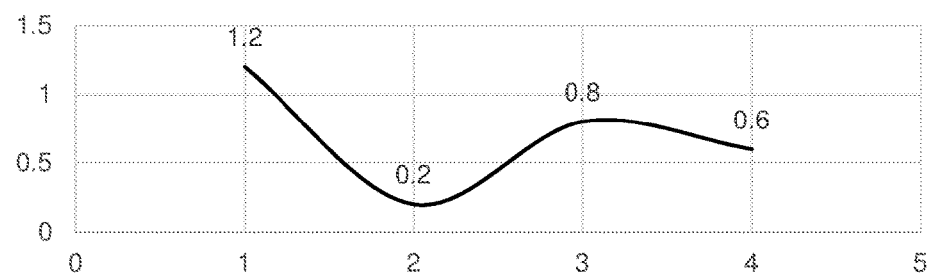
FIG. 5B depicts a diagram of example Z values after the Gaussian process prior in accordance with an embodiment of the present disclosure.

FIG. 5A depicts a diagram of example Z values before Gaussian process prior in accordance with an embodiment of the present disclosure. FIG. 5B depicts a diagram of example Z values after Gaussian process prior in accordance with an embodiment of the present disclosure. It can be seen that violent fluctuation shown in FIG. 5A is smoothed after Gaussian process prior.

Back to FIG. 4, the system 400 also includes differential privacy mechanism 423. Differential privacy mechanism 423 is a mechanism for sharing information about a dataset by describing the patterns of groups within the dataset while withholding information about individuals in the dataset. In more detail, differential privacy mechanism 423 can update the latent space Z 415 with differential privacy noise (hereinafter DP noise).

Injecting DP noise avoids the original EHR dataset X 411 being exposed from constantly testing the Variational Autoencoder (VAE) module 410 and stochastic process prior module 421. A malicious user, intending to find the original EHR dataset X 411, can feed a large number of testing data to Variational Autoencoder (VAE) module 410, obtain returned Z values in the latent space Z 415, compare the difference of the latent space Z 415 before the testing data being fed, and then figure out the original EHR dataset X 411. On one hand, with more DP noise being injected, security level of the original EHR dataset X 411 will be increased. On another hand, more DP noise being injected can result to the larger distortion of the latent space Z 415, while less DP noise being injected can result to a less distortion of the latent space Z 415. Therefore, a balance should be kept between the demand for increased security level and data distortion. In order to maintain the balance, a privacy budget ε (which can be, for example, a value between 1-10) can be used to measure to what degree DP noise need to be injected. The smaller the privacy budget ε is, the bigger the DP noise is, and the latent space Z will lack more fidelity. The bigger the privacy budget ε is, the less the DP noise and the fidelity of latent space Z will be kept. Therefore, the privacy budget ε could be set as a value between its minimum and maximum value, for example, a value between 4-5. It can be understood that injecting DP noise into the latent space Z 415 can be achieved by any existing or newly developed mechanism.

For original EHR data X 411 represented by discrete values, the latent space Z 415 is also going to be represented by discrete values. The differential privacy mechanism module 423 can update the latent space Z 415 by an exponential mechanism based on the received privacy budget ε, which could be decided by prior experience/knowledge. For example, Z values in the latent space Z 415, such as $$z_{1, j_{j=1}^{A}} = [0,1,0,1],$$

could be flipped to $$z_{1, j_{j=1}^{A}} = [0,1,1,1]$$

after DP noise being injected. Finally, updated latent space Z 415' could be slightly different from the original latent space Z 415, which ensures the fidelity of data with increased security level.

Figure 5C:
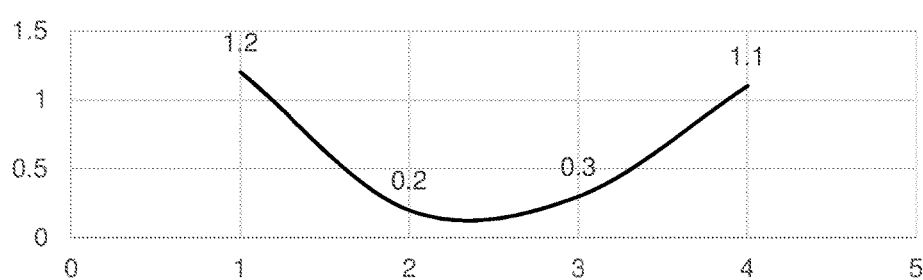
FIG. 5C depicts a diagram of example Z values after DP noise being injected in accordance with an embodiment of the present disclosure.

Similarly, for the original EHR data 411 represented by continuous values, the latent space Z 415 can also be represented by continuous values. The differential privacy mechanism module 423 can update the latent space Z 415 by a Laplace mechanism based on the received privacy budget ε. FIG. 5C depicts a diagram of example Z values after DP noise being injected in accordance with an embodiment of the present disclosure. It can be observed that Z values are updated from FIG. 5B to 5C after DP noise was injected.

Back to FIG. 4, the decoder 417 can reconstruct synthetic EHR dataset X' 419 based on the updated latent space Z 415'. Examples of EHR dataset X' 419 reconstructed from the same Z values $$z_{1, j_{j=1}^{A}} = [3,2,1,0]$$

could be shown as following:

$$x'_{11} = \begin{bmatrix} 180 \\ 6.7 \\ 0.93 \end{bmatrix}$$

$$x'_{12} = \begin{bmatrix} 115 \\ 6.9 \\ 0.96 \end{bmatrix}$$

$$x'_{13} = \begin{bmatrix} 118 \\ 5.3 \\ 0.99 \end{bmatrix}$$

$$x'_{14} = \begin{bmatrix} 110 \\ 5.4 \\ 1.23 \end{bmatrix}$$

$$x'_{21} = \begin{bmatrix} 195 \\ 6.8 \\ 0.92 \end{bmatrix}$$

$$x'_{22} = \begin{bmatrix} 115 \\ 7.0 \\ 0.95 \end{bmatrix}$$

$$x'_{23} = \begin{bmatrix} 115 \\ 5.4 \\ 0.98 \end{bmatrix}$$

$$x'_{24} = \begin{bmatrix} 115 \\ 5.4 \\ 1.20 \end{bmatrix}$$

It is noted that although the reconstructed synthetic EHR dataset X' 419 is in the same dimensionality of original EHR dataset X 411, the amount of data in synthetic EHR dataset X' 419 could be larger than that of the original EHR dataset X 411, because multiple X' values can be reconstructed from the same Z values in the latent space Z 415. Therefore, the VAE module 410 can achieve the purpose of data expansion to provide more data for later analysis.

It should be noted that both Laplace mechanism and Exponential mechanism are illustrated for example in above embodiments without suggesting any limitation. Other existing or newly developed mechanism can also be used for achieving differential privacy mechanism module 423.

Figure 6A:
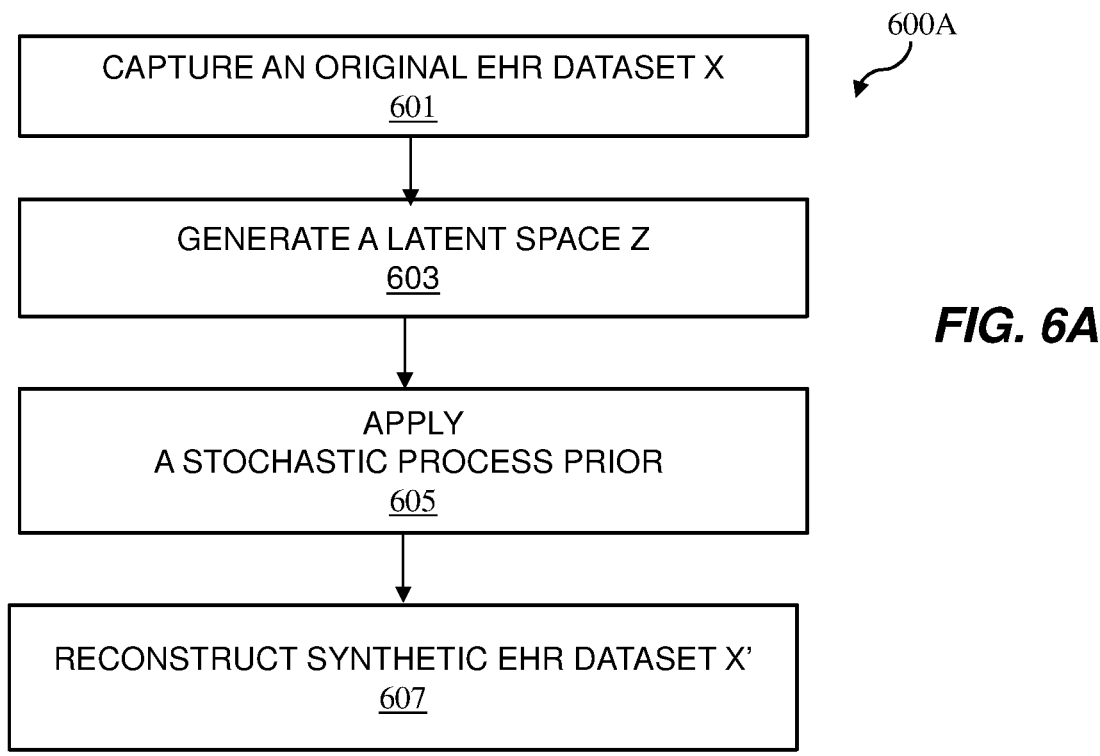
FIG. 6A depicts a flowchart of EHR data synthetization method in accordance with an embodiment of the present disclosure.

FIG. 6A depicts a flowchart of EHR data synthetization method 600A in accordance with an embodiment of the present disclosure. At step 601, an original EHR dataset X can be captured, wherein X can include multiple EHR data from multiple patients. At step 603, a latent space Z is generated from the original EHR dataset X, wherein dimensionality of Z is lower than that of X. For example, above 3×1 dataset X can be reduced into 1×1 dataset Z. At step 605, a stochastic process prior can be applied to the latent space Z to make sure the Z values can comply with characteristics of time series. At step 607, synthetic EHR dataset X' can be reconstructed from the latent space Z, wherein synthetic HER dataset X' is similar but different from original EHR dataset X.

In accordance with embodiments of this disclosure, if the latent space Z comprises discrete values, at the step 605, state space S and a transition rate matrix Q can be further received, and Markov process prior can be applied as the stochastic process prior to the latent space Z 415 based on the state space S and the transition rate matrix Q.

In accordance with embodiments of this disclosure, if the latent space Z 415 comprises continuous values, at the step 605, a covariance and a mean can be received, and a Gaussian process prior can be applied as the stochastic process prior to the latent space Z 415 based on the covariance and the mean.

Figure 6B:
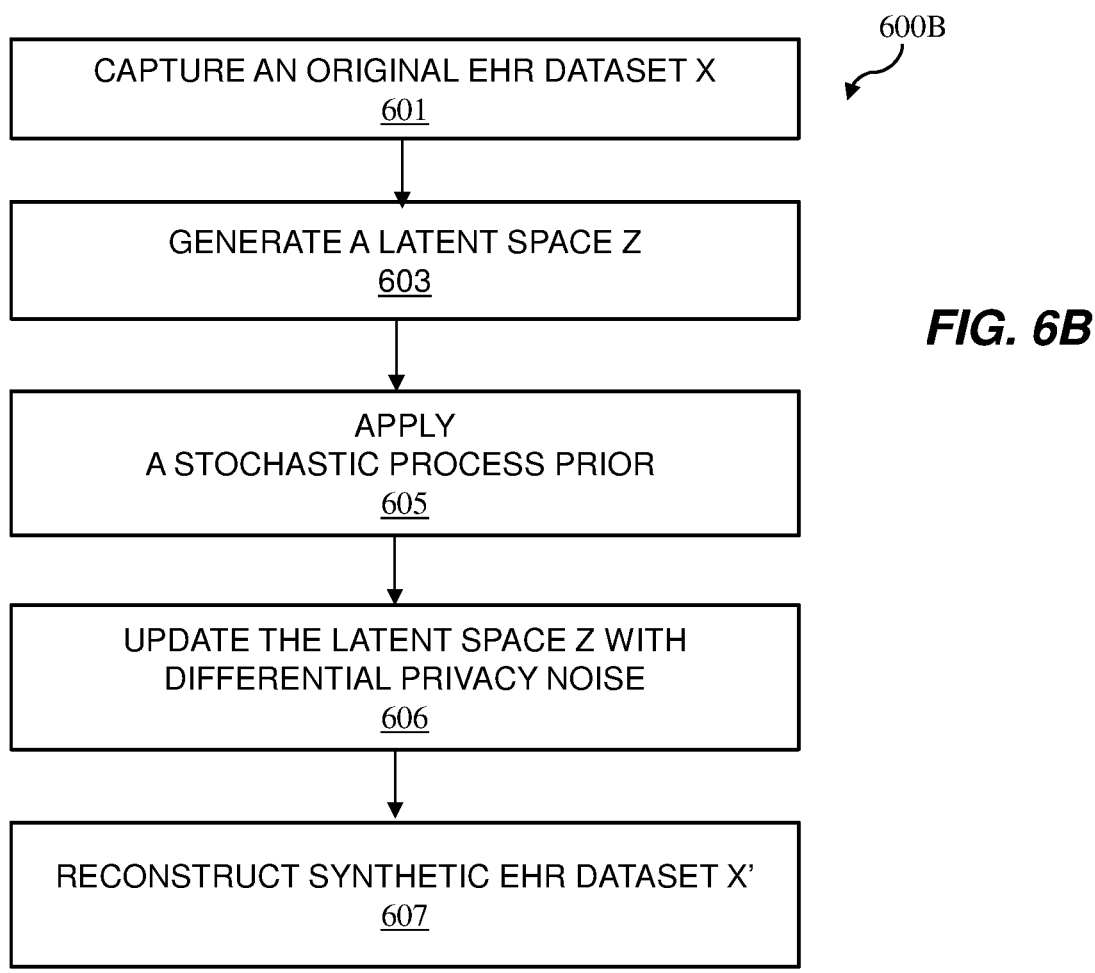
FIG. 6B depicts a flowchart of EHR data synthetization method in accordance with another embodiment of the present disclosure.

FIG. 6B depicts a flowchart of EHR data synthetization method 600B in accordance with another embodiment of the present disclosure. Compared with the method 600A in FIG. 6A, an additional step 606 is further involved, while all other steps remain unchanged. Repetitive description of like elements employed in other embodiments described herein is omitted for sake of brevity. At step 606, in order to increase security and protect privacy of the original EHR dataset X 411, the latent space Z 415 can be updated with DP noise.

If the latent space Z 415 comprises discrete values, the step 606 can further comprise receiving a privacy budget ε, and updating the latent space Z 415 by an exponential mechanism based on the received privacy budget ε. It is well understood that the exponential mechanism is provided here for illustration purpose without suggesting any limitation. Other mechanism, either existing or newly developed, that can inject DP noise to discrete values can also be used.

If the latent space Z 415 comprises continuous values, the step 606 can further comprise receiving a privacy budget ε, and updating the latent space Z 415 by a Laplace mechanism based on the received privacy budget ε. It is well understood that the Laplace mechanism is provided here for illustration purpose without suggesting any limitation. Other mechanism, either existing or newly developed, that can inject DP noise to continuous values can also be used.

It should be noted that the method/system/computer program product for EHR data synthetization according to embodiments of this disclosure could be implemented by computer system/server 12 of FIG. 1.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for electronic health record (EHR) data synthetization, comprising:
    capturing, by one or more processing units, an original EHR dataset;
    generating, by one or more processing units in a variational autoencoder module, a latent space from the original EHR dataset, wherein;
        dimensionality of the latent space is lower than that of the original EHR dataset; and
        the latent space comprises discrete values;
    applying, by one or more processing units, a stochastic process prior to the latent space, wherein applying the stochastic process prior further comprises:
        receiving, by one or more processing units, a state space and a transition rate matrix; and
        applying, by one or more processing units, Markov process prior as the stochastic process prior to the latent space based on the state space and the transition rate matrix for the discrete values to consider characteristics of a time series of the original EHR dataset;
    reconstructing, by one or more processing units in the variational autoencoder module, a synthetic EHR dataset from the latent space in response to being applied with the stochastic process prior;
    comparing, by one or more processing units, the synthetic EHR dataset to the original EHR dataset; and
    backpropagating, by one or more processing units, error through the variational autoencoder module to update weights to train the variational autoencoder module.

2. The method of claim 1, wherein the latent space further comprises continuous values that are separated by shorter amounts of time than the discrete values, and the applying stochastic process prior further comprises:
    receiving, by one or more processing units, a covariance and a mean; and
    applying, by one or more processing units, a Gaussian process prior as the stochastic process prior to the latent space based on the covariance and the mean.

3. The method of claim 1, further comprising:
    updating, by one or more processing units, the latent space with differential privacy noise.

4. The method of claim 3, wherein the latent space comprises discrete values, and the updating latent space further comprises:
    receiving, by one or more processing units, a single privacy budget; and
    updating, by one or more processing units, the latent space by an exponential mechanism based on the single privacy budget.

5. The method of claim 3, wherein the latent space comprises continuous values, and the updating latent space further comprises:
    receiving, by one or more processing units, a single privacy budget; and
    updating, by one or more processing units, the latent space by a Laplace mechanism based on the single privacy budget.

6. The method of claim 1, wherein reconstructing the synthetic EHR dataset from the latent space comprises multiple iterations of reconstructing such that the synthetic EHR dataset is larger than the original EHR dataset.

7. A computer program product for electronic health record (EHR) data synthetization, comprising:
    a computer readable storage medium having program instructions embodied therewith, the program instructions being executable by a computer to cause the computer to perform a method comprising:
    capturing an original EHR dataset;

generating, by a variational autoencoder module, a latent space from the original EHR dataset, wherein:
dimensionality of the latent space is lower than that of the original EHR dataset; and
the latent space comprises discrete values;
applying a stochastic process prior to the latent space, wherein applying the stochastic process prior further comprises:
receiving a state space and a transition rate matrix; and
applying Markov process prior as the stochastic process prior to the latent space based on the state space and the transition rate matrix for the discrete values to consider characteristics of a time series of the original EHR dataset;
reconstructing, by the variational autoencoder module, a synthetic EHR dataset from the latent space after being applied with the stochastic process prior;
comparing, by one or more processing units, the synthetic EHR dataset to the original EHR dataset; and
backpropagating, by one or more processing units, error through the variational autoencoder module to update weights to train the variational autoencoder module.

8. The computer program product of claim 7, wherein the latent space further comprises continuous values that are separated by shorter amounts of time than the discrete values, and the applying stochastic process prior further comprises:
receiving a covariance and a mean; and
applying a Gaussian process prior as the stochastic process prior to the latent space based on the covariance and the mean.

9. The computer program product of claim 7, the method further comprising:
updating the latent space with differential privacy noise.

10. The computer program product of claim 9, wherein the latent space comprises discrete values, and the updating latent space further comprises:
receiving a single privacy budget; and
updating the latent space by an exponential mechanism based on the received single privacy budget.

11. The computer program product of claim 9, wherein the latent space comprises continuous values, and the updating latent space further comprises:
receiving a single privacy budget; and
updating the latent space by a Laplace mechanism based on the received single privacy budget.

12. The computer program product of claim 7, wherein reconstructing the synthetic EHR dataset from the latent space comprises multiple iterations of reconstructing such that the synthetic EHR dataset is larger than the original EHR dataset.

13. A computer system for electronic health record (EHR) data synthetization, comprising:
one or more processors;
a memory coupled to at least one of the processors; and
a set of computer program instructions stored in the memory and executed by at least one of the processors to perform a method comprising:
capturing an original EHR dataset;
generating, by a variational autoencoder module, a latent space from the original EHR dataset, wherein:
dimensionality of the latent space is lower than that of the original EHR dataset; and
the latent space comprises discrete values;
applying a stochastic process prior to the latent space, wherein applying the stochastic process prior further comprises:
receiving state space and a transition rate matrix; and
applying Markov process prior as the stochastic process prior to the latent space based on the state space and the transition rate matrix for the discrete values to consider characteristics of a time series of the original EHR dataset;
reconstructing, by the variational autoencoder module, a synthetic EHR dataset from the latent space after being applied with the stochastic process prior;
comparing, by one or more processing units, the synthetic EHR dataset to the original EHR dataset; and
backpropagating, by one or more processing units, error through the variational autoencoder module to update weights to train the variational autoencoder module.

14. The computer system of claim 13, wherein the latent space further comprises continuous values that are separated by shorter amounts of time than the discrete values, and the applying stochastic process prior further comprises:
receiving a covariance and a mean; and
applying a Gaussian process prior as the stochastic process prior to the latent space based on the covariance and the mean.

15. The computer system of claim 13, the method further comprising:
updating the latent space with differential privacy noise.

16. The computer system of claim 15, wherein the latent space comprises discrete values, and the updating latent space further comprises:
receiving a single privacy budget; and
updating the latent space by an exponential mechanism based on the received single privacy budget.

17. The computer system of claim 15, wherein the latent space comprises continuous values, and the updating latent space further comprises:
receiving a single privacy budget; and
updating the latent space by a Laplace mechanism based on the received single privacy budget.

18. The computer system of claim 13, wherein relevant features of the original EHR dataset are stored in a compressed representation in the latent space.

19. The computer system of claim 18, wherein the synthetic EHR dataset is a decompressed representation of the compressed representation of the original EHR dataset stored in the latent space.

20. The computer system of claim 13, wherein reconstructing the synthetic EHR dataset from the latent space comprises multiple iterations of reconstructing such that the synthetic EHR dataset is larger than the original EHR dataset.

* * * * *